United States Patent [19]
Shersher

[11] 3,973,278
[45] Aug. 10, 1976

[54] ARTIFICIAL HIP-JOINT

[76] Inventor: Yakov Isaevich Shersher, 1 Degtyarny proezd, 3, kv. 42, Saratov, U.S.S.R.

[22] Filed: June 27, 1975

[21] Appl. No.: 591,111

[30] Foreign Application Priority Data
July 8, 1974 U.S.S.R. .............................. 2036651

[52] U.S. Cl. .................................. 3/1.912; 128/92 C
[51] Int. Cl.² ............................................ A61F 1/24
[58] Field of Search ........................ 3/1, 1.9–1.913; 128/92 C, 92 CA

[56] References Cited
UNITED STATES PATENTS

| | | | |
|---|---|---|---|
| 3,102,536 | 9/1963 | Rose et al. ...................... | 128/92 CA |
| 3,656,184 | 4/1972 | Chambers ..................... | 128/92 CA X |
| 3,818,512 | 6/1974 | Shersher .......................... | 3/1.912 |
| 3,820,167 | 6/1974 | Sivash ............................ | 3/1.912 |
| 3,848,272 | 11/1974 | Noiles ............................ | 3/1.913 |

Primary Examiner—Ronald L. Frinks
Attorney, Agent, or Firm—Steinberg & Blake

[57] ABSTRACT

A hip-joint replacement having an endoprosthesis of the acetabulum and an endoprosthesis of the proximal portion of the femur connected with the endoprosthesis of the acetabulum, the endoprosthesis of the proximal portion of the femur comprising an intramedullar nail, a neck into which said pin smoothly turns, and a spherical head secured on said neck. On the end of the neck there is formed a slot for receiving a taper pin whose widening portion faces outward, the height of the taper pin exceeding the depth of the slot formed in the neck. The spherical head has a slot broadening toward the interior of the head which serves to accommodate said neck with said taper pin. The proposed principle of connection of the neck with the head of the endoprosthesis of the proximal portion of the femur improves the reliability and strength of the artificial hip-joint, while simultaneously providing a simpler manufacturing procedure.

1 Claim, 2 Drawing Figures

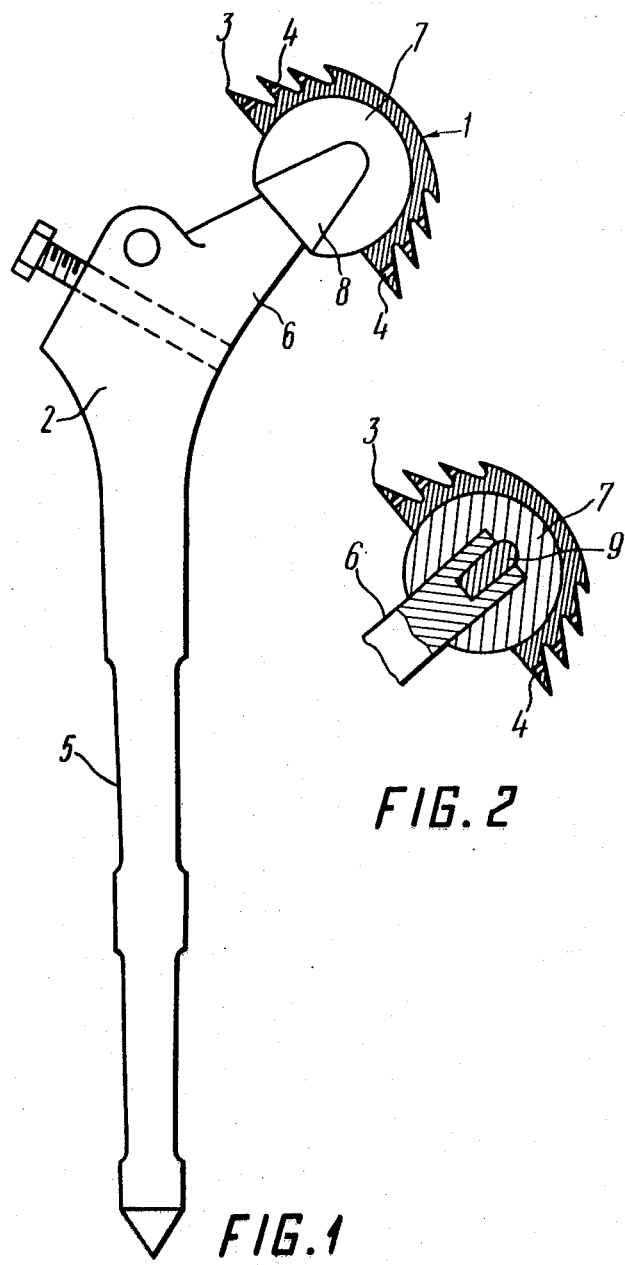

ARTIFICIAL HIP-JOINT

The present invention relates to artificial hip-joints employed in surgical intraarticulated endoprosthetic replacement.

The invention may be employed to restore hip-joint mobility lost in the aftermath of Bekhterev's disease, arthritis deformans, arthritis infectiosa, aceptic necrosis of the femoral head and some femoral neck fractures.

It is known in the art to employ an artificial hip-joint which comprises an endoprosthesis of the acetabulum and an endoprosthesis of the proximal portion of the femur, the two endoprostheses being interconnected. The endoprosthesis of the acetabulum is formed as a seat whereof the exterior surface is formed as tierwise arranged blades with sharp edges and holes formed therein wherethrough burgeoning bony tissue may advance. The endoprosthesis of the proximal portion of the femur comprises an intramedullar nail turning into a neck carrying a spherical head secured thereon. The spherical head of the endoprosthesis of the proximal portion of the femur forms an articulated joint with the seat of the endoprosthesis of the acetabulum which reliably provides for the mobility of the artificial hip-joint.

The head of the endoprosthesis of the proximal portion of the femur has a cylindrical slot formed therein which assists in shrink-fitting said head over the neck of the endoprosthesis of the proximal portion of the femur.

As a result of said shrink-fitting procedure, the head of the endoprosthesis is deformed at the base thereof, so that the head of the endoprosthesis must be subjected to additional machining, for otherwise the spherical head of the endoprosthesis of the proximal portion of the femur will get stuck in the seat of the endoprosthesis of the acetabulum, with resultant loss of mobility of the artificial hip-joint. It should be further noted that this machining procedure is only possible if the artificial hip-joint has a split design.

The additional machining procedure adds to the complexity of the process of manufacturing the artificial hip-joint and yet fails to reliably provide for the mobility of such artificial joint.

It is likewise known in the art to employ an artificial hip-joint wherein the head of the endoprosthesis of the proximal portion of the femur is coupled with the neck of that same endoprosthesis with the aid of a clamp screw introduced into the neck by way of a through hole formed in the head.

Apart from being unreliable, such principle of connection cannot be employed in the articulated joints of artificial hip-joints.

It is an object of the present invention to obviate said disadvantages.

It is a further object of the present invention to provide an artificial hip-joint distinguished by virtue of improved reliability and a higher degree of mobility as against the similar prior art hip-joints.

It is another object of the present invention to provide an artificial hip-joint which can be manufactured in a simpler manner than similar prior art joints.

The foregoing objects are attained by providing an artificial hip-joint, comprising an endoprosthesis of the acetabulum formed as a seat whereof the exterior surface is formed as tierwise arranged blades with sharp edges and holes formed therein wherethrough burgeoning bony tissue may advance and an endoprosthesis of the proximal portion of the femur connected with the former endoprosthesis of the acetabulum, said endoprosthesis of the proximal portion of the femur comprising a spherical head, a neck secured in a slot formed in the spherical head, and an intramedullar nail. In accordance with the invention, the neck of the endoprosthesis of the proximal portion of the femur has an axial slot formed therein for receiving a taper pin whereof the widening portion faces outward and whereof the height exceeds the depth of said slot, and the slot formed in said spherical head widens toward the interior of the head thereby aiding in coupling said neck with said head.

The proposed principle of connection of the neck and the head of the endoprosthesis of the proximal portion of the femur makes it possible to improve the reliability and strength of the artificial hip-joint and simplifies the manufacturing procedure, for the artificial hip-joint of this invention dispenses with the previously indispensable machining of the spherical head of the endoprosthesis of the proximal portion of the femur after the head has been connected with the neck.

Other objects and advantages of the present invention will become obvious from the following detailed description of the proposed artificial hip-joint taken in conjunction with the accompanying drawings, wherein:

FIG. 1 is a general view of an artificial hip-joint, in accordance with the present invention; and FIG. 2 is a longitudinal axial sectional view of the site of connection of an endoprosthesis of the acetabulum with an endoprosthesis of the proximal portion of the femur.

Referring now to the drawings, the artificial hip-joint (FIGS. 1 and 2) of the present invention comprises an endoprosthesis 1 (FIGS. 1 and 2) of the acetabulum connected with an endoprosthesis 2 (FIG. 1) of the proximal portion of the femur.

The endoprosthesis 1 of the acetabulum is formed as a seat whereof the exterior surface is formed as tierwise arranged blades 3 (FIGS. 1 and 2) with sharp edges and holes 4 (FIGS. 1 and 2) wherethrough burgeoning bony tissue may advance. The blades 3 and the holes 4 are designed for securing the endoprosthesis 1 of the acetabulum to the patient's bone without recourse to a cementing agent. The interior surface of the endoprosthesis 1, viz. of the seat, is spherical with the cavity height being greater than the radius but smaller than the diameter.

The endoprosthesis 2 of the proximal portion of the femur comprises an intramedullar nail 5 (FIG. 1) which smoothly turns into a neck 6 (FIGS. 1 and 2) carrying a spherical head 7 (FIGS. 1 and 2) secured thereon. On the exterior surface of the head 7 there are formed two flats 8 (FIG. 1). The spherical head 7 of the endoprosthesis 2 of the proximal portion of the femur forms an articulated joint with the seat of the endoprosthesis 1 of the acetabulum, said articulated joint assuring a high degree of mobility of the artificial hip-joint.

In the spherical head 7 of the endoprosthesis 2 of the proximal portion of the femur there is formed a slot for accomodating the neck 6. In accordance with the present invention, said slot is to widen toward the interior of the head 7.

In accordance with the present invention, a slot is to be axially formed in the neck 6 of the endoprosthesis 2 of the proximal portion of the femur, said slot being designed to accommodate a taper pin 9 (FIG. 2). The taper pin 9 is to be so disposed in said slot formed in the neck 6 that the widening portion of the pin 9 faces outward. Besides, the proposed taper pin 9 is to have a height exceeding the depth of said slot in the neck 6 by a value ensuring a good fit of the neck 6 to the head 7 as the head 7 is shrink-fitted over the neck 6 with the previously inserted taper pin 9. Said fit of the neck 6 to the head 7 is further provided for by the taper pin 9.

The use of the taper pin 9 permits widening the peripheral portion of the neck 6, thereby preventing deformation of the head 7 at the base thereof in the course of press-fitting.

Said taper pin 9 as well as said slots formed in the above-described manner enable the neck 6 to be securely connected with the head 7, preventing any possibility of deformation of the head 7, which simplifies the process of manufacturing the proposed artificial hip-joint.

The artificial hip-joint of the present invention is installed as follows: the tissues on the exterior surface of the patient's thigh are incised, the trochanter major is cut off and lifted by the muscular pedicle, and the articular cavity is dissected. The femoral head is dislocated into the wound and resected together with neck at the latter's base. The nail 5 of the endoprosthesis 2 of the proximal portion of the femur is driven into the femoral medullary canal, the endoprosthesis 1 of the acetabulum is impacted into the patient's acetabulum, the sharp edges of the blades 3 with the holes 4 wherethrough burgeoning bony tissue may advance getting embedded into the bony tissue of the patient's acetabulum and thereby providing for a secure connection.

After this the patient's trochanter major is set in its place and the wound is sutured.

The proposed design of the artificial hip-joint, with the head 7 being secured to the neck 6 in the proposed way, and the geometry of said slots prevent deformation of the spherical head 7 of the endoprosthesis 2 of the proximal portion of the femur. After the prosphetic replacement procedure with the use of the artificial hip-joint of this invention the patient retains an excellent degree of hip-joint freedom.

What is claimed is:

1. An artificial hip-joint, comprising an endoprosthesis of the acetabulum formed as a seat whereof the exterior surface is formed as tierwise arranged blades with sharp edges having holes formed therein wherethrough burgeoning bony tissue may advance; and endoprosthesis of the proximal portion of the femur articulated with said endoprosthesis of the acetabulum; a spherical head of said endoprosthesis of the proximal portion of the femur; a slot formed in said spherical head and broadening toward the interior of said head; a neck of said endoprosthesis of the proximal portion of the femur installed in said slot formed in said spherical head; a slot axially formed at the end of said neck; a taper pin installed in said slot formed in said neck with the widening portion of said taper pin facing outward, the height of said taper pin exceeding the depth of said slot formed in the neck; an intramedullar nail of said endoprosthesis of the proximal portion of the femur which smoothly turns into said neck, said spherical head serving to provide said articulation of said endoprosthesis of the acetabulum with said endoprosthesis of the proximal portion of the femur.

* * * * *